(12) United States Patent
Hvalsøe et al.

(10) Patent No.: US 12,364,861 B2
(45) Date of Patent: Jul. 22, 2025

(54) SYSTEM FOR ELECTRICAL STIMULATION OF NERVES

(71) Applicant: INNOCON MEDICAL APS, Aalborg SV (DK)

(72) Inventors: Torsten Fjeldgaard Hvalsøe, Aalborg (DK); Dianna Marsk Knudsen, Løgstør (DK); Jesper Nielsen, Klarup (DK)

(73) Assignee: INNOCON MEDICAL APS, Aalborg (DK)

( * ) Notice: Subject to any disclaimer, the term of this patent is extended or adjusted under 35 U.S.C. 154(b) by 920 days.

(21) Appl. No.: 17/431,701

(22) PCT Filed: Feb. 17, 2020

(86) PCT No.: PCT/DK2020/050039
§ 371 (c)(1),
(2) Date: Aug. 17, 2021

(87) PCT Pub. No.: WO2020/164677
PCT Pub. Date: Aug. 20, 2020

(65) Prior Publication Data
US 2022/0134105 A1    May 5, 2022

(30) Foreign Application Priority Data

Feb. 17, 2019    (DK) .................. 2019 00209

(51) Int. Cl.
*A61N 1/36* (2006.01)
*A61H 23/02* (2006.01)
*A61N 1/05* (2006.01)

(52) U.S. Cl.
CPC ......... *A61N 1/36017* (2013.01); *A61H 23/02* (2013.01); *A61N 1/0502* (2013.01);
(Continued)

(58) Field of Classification Search
CPC .............. A61N 1/36017; A61N 1/0502; A61N 1/0558; A61N 7/00; A61N 2007/0026;
(Continued)

(56) References Cited

U.S. PATENT DOCUMENTS 11,850,434 B2 * 12/2023 Knudsen ............ A61N 1/37518
2004/0172095 A1    9/2004 Jenkins
(Continued)

FOREIGN PATENT DOCUMENTS

WO    2019034223 A1    2/2019

OTHER PUBLICATIONS

Written Opinion of the International Searching Authority issued in PCT/DK2020/050039, dated May 29, 2020, 6 pgs.
(Continued)

*Primary Examiner* — Mark W. Bockelman
(74) *Attorney, Agent, or Firm* — HOLLAND & HART LLP

(57) ABSTRACT

In a system for electrical stimulation of nerves of a living being a pulse generator is configured to provide a sequence of electrical and/or vibration pulses to at least one electrode and/or vibration generator that are maintained in close proximity to the nerve of interest with the use of means for securing the electrode to the skin or tissue of the living being.

20 Claims, 3 Drawing Sheets

(52) U.S. Cl.
CPC .... *A61N 1/0558* (2013.01); *A61H 2201/0103* (2013.01); *A61H 2201/10* (2013.01)

(58) Field of Classification Search
CPC ................ A61N 1/36007; A61H 23/02; A61H 2201/0103; A61H 2201/10; A61H 19/30; A61H 19/32; A61H 19/34; A61H 21/00; A61H 39/002; A61H 39/007; A63B 23/20
See application file for complete search history.

(56) References Cited

U.S. PATENT DOCUMENTS

| | | | |
|---|---|---|---|
| 2007/0239224 A1 | 10/2007 | Bennett | |
| 2010/0331883 A1* | 12/2010 | Schmitz | A61B 17/320758 |
| | | | 606/279 |
| 2012/0330123 A1 | 12/2012 | Doerr | |
| 2017/0136232 A1 | 5/2017 | Oron | |
| 2020/0222706 A1* | 7/2020 | Knudsen | A61N 1/37518 |
| 2022/0118245 A1* | 4/2022 | Hvalsoe | A61N 1/0496 |

OTHER PUBLICATIONS

International Search Report issued in PCT/DK2020/050039, dated May 29, 2020, 3 pgs.

* cited by examiner

SYSTEM FOR ELECTRICAL STIMULATION OF NERVES

CROSS-REFERENCE TO RELATED APPLICATIONS

This is a national phase application of International Application No. PCT/DK2020/050039, filed 17 Feb. 2020, which claims the benefit of Danish Patent Application No. PA201900209, filed 17 Feb. 2019, the disclosures of which are incorporated, in their entireties, by this reference.

TECHNICAL FIELD

The present invention is generally concerned with stimulation of nerves.

BACKGROUND OF THE INVENTION

Stimulation of nerves is known to have a positive effect on a variety of illnesses that derives from a defective nervous system. Electrical stimulation of the vagus nerve has as an example proven to be an efficacious treatment of epilepsy. It has also been shown that stimulation of the genital nerves can have a positive effect in the treatment of fecal and urinary incontinence. Tactile or mechanical stimulation is a natural means of stimulation, and it has previously been shown that one can stimulate the nerves of the pelvic floor by means of transcutaneous mechanical nerve stimulation (TMNS) done through vibration.

For the sake of explaining the invention, the treatment of incontinence has been chosen to exemplify the advantageous features but should not be taken as limiting for the scope of the invention for which the inventive concept could be carried out in order to stimulate nerves contained in the human body without specifying the reason for stimulating the specific nerve.

Overactive bladder (OAB) syndrome is a highly prevalent condition worldwide, particularly in the general population above 40 years, where prevalence has been reported to be about 17%. Frequency (85%) is the most commonly reported symptom, followed by urgency (54%) and urge urinary incontinence (36%). These symptoms adversely affect patients' quality of life due to social and hygienic difficulties. Upper urinary tract damage caused by sustained high intravesical pressures and repeated bladder infections is another concern that causes morbidity, hospitalization or even death. Conventional treatment is typically based on drugs with dose-limiting systemic side effects.

Fecal incontinence (FI) is also highly frequent with prevalence between 5-15% in the general population. It is commonly defined as the involuntary loss of solid or liquid feces or mucus and is a disabling symptom, which can have a devastating impact on quality of life, as its effects may include embarrassment, social isolation, and even loss of employment. Conservative treatment may be dietetic measures, various pharmacological agents, anorectal rehabilitation, and transanal irrigation.

In both OAB and FI surgical destructive interventions may be considered if patients are refractory to conventional treatment options but complication rates are often high. Alternative treatment options should be considered in refractory patients to avoid destructive surgery.

Continuous or intermittent electrical stimulation of the sacral nerves is known to be effective in the treatment of a variety of pelvic disorders, such as OAB and FI (InterStim® Therapy, Medtronic, MN, USA). InterStim® Therapy is based on electrical stimulation of the sacral root/s using a medical lead connected to an implanted pulse generator. Electrical stimulation of the sacral root/s activates sacral somatic afferents that modulate the sacral reflex pathways. This effect is also known as neuromodulation and has been shown to reduce the symptoms of OAB and FI.

However, a completely implantable system is quite expensive in both hardware costs and for the act of implanting the whole system into the living being. Additionally, implanting a medical system into a living being should only be offered if alternative solutions available have failed. There seems to be a need for a simpler and affordable solution that provides an acceptable therapy to the outlined problem without the need for fully implantable systems.

US 2015/0352357 A1 to Medtronic present a solution providing a surface electrode in two variants. One for male use and one for female use, each variant designed with attempt to take advantage of the specific shape of the genitals of the genders and attempting to arrange electrodes that target the genital nerves. However, the disclosure does not explain how the electrodes are arranged and secured in a desired position where an effective electrical charge can be addressed towards the genital nerves.

Typically, surface electrodes are patch-type electrodes utilizing an adhesive and conductive hydrogel, with various supportive scrims and fabrics for strength and structural support. Due to the necessity of supportive scrims and wire meshes most types of such electrodes becomes relatively stiff and rigid. This has the effect that the electrodes looseness from the skin to which they are applied, especially during activity, or when applied to uneven structures or moistened skin such as on the genitals or at the Achilles tendon, leading to loss of functionality.

Thus, there is a need for an improvement that provides a stable electrode interface towards the genital nerves and provides a secure arrangement through the skin of the human being at the position of interest in close proximity to the genital nerves.

DESCRIPTION OF THE INVENTION

It is an object of the embodiments of the present invention to provide a system, which overcomes or at least reduces the above-mentioned disadvantages.

The present invention provides a solution, where the electrode/s and/or vibration generator/s is fixated and secured by mechanical expansion of the electrode unit body so that it is kept in the constant distance and with the constant orientation with regard to the position of the part of the nerve and/or its branches intended to be treated, thus the electrode and/or vibration generator/s and the nerve being positioned mutually in the same stable position with regard to each other, even during exercise.

The invention discloses a stimulation media fixation unit which when exclusively providing electrical stimulation constitutes an electrode fixation unit, and when exclusively providing mechanical stimulation constitutes a vibration generator fixation unit. The invention further includes variants of the stimulation media fixation unit where electrical and/or mechanical stimulation can be provided simultaneously. In the event an electrode is present as part of the stimulation media fixation unit, then it is comprehended as an electrode fixation unit even though it also features a vibrations generator.

A ground, or anode electrode may be positioned in close proximity of the cathode electrode/stimulating electrode, or distant, eventually as a patch type/skin electrode. The latter may provide an option for a relative larger electrode attached to or integrated into the electrode fixation unit, thus eliminating many of the concerns to be addressed for the cathode electrode, including being positioned on less challenging parts of the body, and providing options for freedom of positioning at convenience of the user. However, some male users may have body hair covering most of the abdomen and may therefore prefer bipolar designs rather than larger return patch type electrodes. Daily handling of a bipolar electrode is advantageous, as the patch type electrode is then fully discarded. Therefore, the bipolar configuration is considered a superior design in most use-cases.

The application may require either quick-onset of the stimulation if/when requested, continuous stimulation during day and/or night, including periodic therapy sessions, depending of the clinically supported setup for the specific patient/user. Thus, the reliability of the fixation is of crucial importance for the product and may be a different use scenario compared to many available applications.

An important aspect is the freedom of movement required during everyday activities such as walking, biking, running or other sports related activities, even further stressing out the critical importance of reliable and comfortable fixation of electrode/s. By further providing the options of combining electrical stimulation with mechanical vibration, additional individual means of setup are thus available to the user's preference/s, and options for selection of specific treatments for the health care provider.

More specifically, fixation of neuromodulation electrodes for methods to treat pelvic floor disorders, such as urinary and fecal incontinence, by stimulation of the left and/or right branches of the dorsal genital nerves, or pudendal nerve afferents, is according to the present invention implemented using an electrode fixation unit inserted through the cutaneous tissue in the region along the penis, and/or at or near the glans of the clitoris, in close proximity of the targeted nerve/s, to support the arrangement of neuromodulation electrodes. Additionally, mechanical vibration as a supportive or alternative means is provided, by built-in vibrations vibration generators in electrode members of the electrode fixation units.

The intended level of fixation prevents the electrodes or means for mechanical vibration from dislocating from the site in the tissue intended to be stimulated. It is intended to be fully integrated into the fibrotic tissue in channel through the skin, i.e. it is not necessarily possible to be removed without a minimally invasive clinical intervention.

In males the dorsal genital nerve is superficial on the dorsal side (i.e. at approximately the upper ¼ of the cross section of the penis) and runs along the length of the shaft of the penis until it reaches the glans, where it fans out.

In females the dorsal genital nerves tend to be close to the mucous membrane (or skin) near the glans of the clitoris between the labium minus and labium majus. Thus, these sites of stimulation are effective for both males and females, since factors such as fat layer and muscle tissue have a significant influence on the activation of the targeted nerves. At the intended site of stimulation, the fat layer is limited, and no muscles cover the nerves.

A reliable means of fixation in the tissue is presented by use of an electrode fixation unit, which is arranged in a formed channel in and out of the skin at the targeted tissue to be stimulated. In general, the disclosure is directed to fixation means of piercing the skin to fixate electrical stimulating electrodes and mechanical stimulating vibration generator/s for delivering of electrical, vibrations or combinations of electrical and vibrations stimulation.

The invention is explained using a variant of the inventive electrode system, capable of holding a vibration micromotor/s, for treating incontinence, but it has to be understood that the concept can be used on the entire body where access to nerves underlying the skin is targeted electrical and/or mechanical stimulation. It could be on the neck for electrically treating epilepsy or it could be on limbs for treating other nervous system impairments, e.g. phantom pains treatment.

In a first aspect, the invention provides A stimulation media fixation unit for electrical and/or mechanical stimulation of nerves of a living being, configured to be arranged in a formed channel in and out of the skin, where the stimulation media fixation unit includes
at least one electrode and/or
at least one vibration generator
configured to be placed in close proximity of a portion of a nerve of a living being, including connection/s to a pulse generator configured to provide a sequence of electrical pulses, and/or mechanical vibrations, to the at least one electrode, or the at least one vibration generator, in order to achieve stimulation of the nerve, where the stimulation media fixation unit has a first end and a second end, where the first end of the stimulation media fixation unit is configured to protrude out of the first end of the formed channel and the second end of the stimulation media fixation unit is configured to protrude out of the second end of the formed channel and where at least one end termination member, configured to be dismantled from and reassembled to the stimulation media fixation unit body, is configured to provide a stop for movement of the stimulation media fixation unit body in at least one direction within the formed channel, where the at least one end termination is positioned outside the first and/or second end of the formed channel, providing a mechanically interlocking mechanism by means of geometry of the end termination for the stimulation media fixation unit further including at least one expanding member and/or at least one adjustable deflectable electrode member specially adapted for providing tissue fixation enhanced through mechanically anchoring in the formed channel by means of expansion.

With the mechanical interlocking mechanism by means of geometry of the end termination, is understood that the end termination has a dimension so large compared to the formed channel that it will not be possible to pull through the channel but will form a stop for the movement that can only be overcome by excess force that possibly will result in trauma to the tissue. Thus, the end termination serves to keep the stimulation media fixation unit in its intended position within the formed channel.

In an embodiment, the system for stimulation of nerves of a living being, includes a stimulation media fixation unit configured to be arranged in a formed channel in and out of the skin, and specially adapted for providing suitable fixation enhanced through mechanically anchoring inside the formed channel by means of expanding member/s and/or adjustable deflectable electrode member/s of at least one electrode or vibration generator/s configured to be placed in close proximity of a portion of a nerve of a living being for stimulation of nerves, and a pulse generator configured to provide a sequence of electrical pulses, and/or mechanical vibrations, to the at least one electrode, or vibration generator/s, in order to achieve stimulation of the nerve, where the stimulation media fixation unit has a first end and a second end, where the first end of the stimulation media fixation unit is configured to protrude out of the first end of the formed channel and the second end of the stimulation media fixation unit is configured to protrude out of the second end of the formed channel and where a stimulation media fixation unit body member is forming the structure of the stimulation media fixation unit into which a vibration generator is included, the electrode fixation unit body configured to include the at least one deflectable electrode member and where at least one end termination member, configured to be dismantled from and reassembled to the electrode fixation unit body, is configured to provide a stop for movement of the stimulation media fixation unit body in at least one direction within the formed channel, where the at least one end termination is positioned outside the first and/or second end of the formed channel, providing a mechanically interlocking mechanism by means of geometry of the end termination for the stimulation media fixation unit and means for controlling or activating the at least one deflective electrode member and/or fixation member when the stimulation media fixation unit is arranged in the formed channel, to form additional means for fixation of the stimulation media fixation unit.

In an embodiment, the deflectable member has a degree of deflection/expansion that is at least 20% relative to the initial dimension it expands. More specifically, in a practical embodiment having a cross section of 5 mm the expansion should be expandable to at least a cross section of 6 mm which is 20%. In a practical embodiment where the cross section is shaped as a square, the square cross section should be expandable to at least 20% compared to the initial dimension being expanded. The same principle applies for other shapes of the expandable member/s.

More expediently, the electrode fixation unit has an elongated form the electrode fixation unit having a first end and a second end where the first end of the electrode fixation unit is configured to protrude out of the formed channel in the tissue through a first perforation of the skin and the second end is configured to protrude out of a second perforation of the skin of the formed channel formed by two interconnected perforations of the skin of a living being when said electrode fixation unit is inserted into said formed channel, into which the fixation unit is configured to be deformed/deflected and thus adapted to mechanically anchor and interlock into the tissue.

In an embodiment, the stimulation media fixation unit, now serving as a vibration generator fixation unit, includes a system for mechanical vibrations stimulation of nerves of a living being, through application of at least one built-in vibration generator providing either linear, rotational, shaking, shivering or inhomogeneous random vibrations and thus configured to mechanically activating the surrounding tissue to trigger nervous response.

In an embodiment, the stimulation media fixation unit is having an internally elongated form and comprising the mechanically expansion mechanism adapted to maintain effective transfer of vibration energy in the form of sinusoidal, linear, rotational, shaking, shivering, haptic movements or random vibration of various amplitudes and frequencies to the targeted tissue, when the stimulation media fixation unit is arranged in the formed channel.

In embodiments of the stimulation media fixation unit not including electrode member/s, the stimulation media fixation unit constitutes a vibration generator fixation unit.

In an embodiment, the vibration generator is a trembler configured to provide vibrations in the form of rotational movements.

In another embodiment the vibration generator is configured to provide vibrations in the form of linear movements.

In an embodiment the vibration generator is a haptic linear resonator.

In yet another embodiment, the vibration generator is a piezo-element.

In embodiments of the invention, the stimulation intensity of the vibration generation is adjustable, within the force range of 0.05 g to 10 g. The mode of action is controlled by frequency and/or amplitude and/or time-span patterns. Some patients prefer the lowest clinically relevant stimulation intensity, where others prefer clearly perceptible levels of stimulation intensity. The clinical performance of the vibration stimulation is depending on the size and/or weight of the electrode fixation unit in which the vibration generator is arranged and the site of implantation, where tissue types and distances to the nerves plays the main roles. For daily use, stimulation intervals can be setup allowing for personal patient-controlled adjustment to meet the individual user's stimulation intensity needs throughout the day. For the exemplified application, where the vibration stimulation is directed to the genital nerves, a host response of triggering sexual arousal as a side-effect is possible, although such host response is not the main focus of this invention.

In an embodiment, electrically stimulation and mechanical vibrations stimulation is provided simultaneously.

In an embodiment, the stimulation media fixation unit is solid-, hollow- or tubular-formed and the cross section is having a triangular, squared or multiple angled cross section until substantially being circular or elliptical formed with even or uneven sized sides and/or with straight or curved sides and having one or multiple cross section areas over the travel length between the first end and second end and where the electrode fixation unit in the longitudinal direction can travel in a straight or bended or curved or spiral or meandering or a combination of said travel form directions.

Examples of multiple cross section areas over the travel length between the first end and second end could be one diameter or circumscribed circle at the first end, and a different or similar diameter or circumscribed circle at the second end, and further different or similar diameter or cross section.

However, in embodiments of the invention, the shape of the stimulation media fixation unit varies with straight or shaped stimulation media fixation unit bodies to complete enclosing rings of various designs and sizes, and diameters or cross-sections. Appreciated configurations of stimulation media fixation units configured to the preference and needs of the individual user have cross sections ranging from a diameter of one millimeter to ten millimeters with a typical shaft curve length in the range of ten to forty millimeters. The curvature of the stimulation media fixation unit body can vary relative to the tissue variation or personal preferences from straight to complete enclosed designs and the said curvature need not be constant. This allows selection of the optimal fit of stimulation media fixation unit for the given therapy planned.

In an embodiment, the stimulation media fixation unit is holding a vibration generator for vibrations stimulation, the stimulation media fixation unit is holding a vibration generator for vibrations stimulation, the stimulation media fixation unit being adapted to forming a hollow tube fitting the vibration generator, said vibration generator and tube not necessarily being circular, the stimulation media fixation unit further comprising a first end termination having an electrical connection to a pulse generator, a second passive end termination fitted at the second end of the stimulation media fixation unit, and at least one deflectable fixation member comprising a nickel titanium based material having shape-memory effect, such as nitinol.

In order to expand when inserted into the formed channel, the deflectable member of the stimulation media fixation unit which comprises a material with shape-memory effect, has a deflection state which is temperature controlled to form itself into the predefined bended shape by means of elevation of the temperature from a level in the range between 0-10 degrees Celsius to a level in the range between 30-40 degrees Celcius, which can be achieved by means of heating by body temperature once positioned into the formed channel.

In more sophisticated embodiments, the stimulation media fixation unit is partly made of an electrical isolating material having electrical conductible sections which serves as electrode member/s suitable for electrical stimulation, having a hollow fixation member with electrical connection/s to the electrode/s running internally in the stimulation media fixation unit and which are terminated in a connector accessible from outside of the stimulation media fixation unit and at least one deflectable/expandable electrode member securing the positioning of the electrode member in the formed channel, by means of tightening the passive end termination member to expand/deflect the deflectable/expandable electrode member to the degree tolerable by the user.

A monopolar stimulation media fixation unit can be provided in this way but also bipolar or multipolar stimulation media fixation units, with options of additionally be fitted with a vibration generator to also provide modes of vibrations stimulation as a stimulation media fixation unit.

In an embodiment, at least one electrode member/s is arranged on the stimulation media fixation unit, and further comprising a deflectable electrode member comprising a nickel titanium based alloy having temperature controlled shape-memory effect, such as nitinol, where the deflectable member is configured to collapse into a closed form in an environment having a temperature level in the range between 0-10 degrees Celsius and thus being prepared for insertion into the formed channel in which it reaches the surrounding temperature of between 30-40 degrees Celsius and thereby return itself into the intended predetermined shape in the formed channel. This behavior is appreciated as designed changes in temperature transforms the deflectable electrode member into these two predetermined shapes/states.

The at least one deflectable member of the stimulation media fixation unit is in various embodiments constituting a passive or non-active fixation member, i.e. not part of, or including an electrode member, where the electrode member is arranged on the stimulation media fixation unit body.

In an embodiment, the at least one deflectable member constitutes an electrode, an anode, a cathode, a non-active fixation means or a combination thereof.

In an embodiment, the deflectable member of the stimulation media fixation unit is configured to be transformed into the intended shaped by control of the deflectable member through turning a threaded end termination member positioned on the stimulation media fixation unit, resultantly shortening the distance between the first end termination and the second end termination and thus providing the deflectable member to bend from its initial shape.

In an embodiment, the at least one deflectable member is arranged on the stimulation media fixation unit an configured to be transformed into predetermined deflected shape through means of shortening the distance between the first end termination and the second end termination by configuring of the first end termination to travel along the stimulation media fixation unit body, where dents positioned on the stimulation media fixation unit body defines the travel distance/s and a spring loaded mechanism in the first end termination member fixates the end termination in at least two positions.

In an embodiment of the stimulation fixation unit, the deflectable member further comprises a balloon arranged with the deflectable member where the deflectable member is configured to be formed by means of the balloon, pressurized for expanding and shaping a ductile deflectable fixation and/or electrode member. The balloon is an integral part of the stimulation media fixation unit, operated from a channel provided through the passive end termination by means of pressurized air or pressurized fluid, operated by use of a suitable syringe, where the preset volume of the syringe controls the level of expansion, or by use of a stand-alone air-pressure system available for and controlled by the physician at the operating theater, and where the at least one deflectable fixation or electrode member is formed as an wholly or partially ball shape, controlled by means of the predefined pressurized balloon element shape, this shape being rounded triangular, squarish or multiple angled cross section until substantially being wholly or partially ball-shaped or ellipsoidal.

In an embodiment of the deflectable member featuring balloon expansion, it includes a flexible sheet or tube element added onto the outside or into the inside of the deflection member, the flexible sheet being special adapted for avoiding tissue integration into the deflection member.

In an embodiment, the flexible conductive element is made of or includes conductive materials and is formed by one or more of plate springs, rod springs, coiled springs, or ductile elements which are at least partially maintaining the deflected shape, once the force providing the deflection is released.

In an embodiment, the flexible non-conductive element being part of the deflectable member comprises bioinert materials and is configured by carefully selecting flexible materials having the properties providing the at least intended degree of deflection, while maintaining stability in the intended deflected position.

In an embodiment, the deflectable electrode members include nonflexible or flexible conductive element/s constituting at least one electrode, at least one elastically deflectable nonconductive member including internal or external electrical wires providing connection to the electrode/s member.

In an embodiment, the at least one end termination member is attached to form closure of the stimulation media fixation unit body into a closed loop, a geometrically closing or an overlapping structure.

In an embodiment, the at least one end termination member is attached to an end of the stimulation media fixation unit body but with a gap between the end termination member and the other end of the stimulation media fixation unit body featuring or not featuring another end termination member. It has to be understood that fixation to the skin does not rely on forming a completely closed loop but on a maintaining a safe fixation which will also be the case even if there is formed a gap.

In an embodiment, the stimulation media fixation unit in the form of an electrode fixation unit is configured to repeatedly be non-destructively dismantled into at least two elements and reassembled, with the main part of the fixation unit initially arranged in the formed channel. In a number of embodiments, the stimulation media fixation unit comprises a biocompatible electrical conductible material such as medical grade 5 titanium, medical grade stainless steel—typical type 316L, platinum, platinum/iridium, medical grade metal alloys such as nitinol and other precious metal alloys suitable for electrical stimulation and/or comprises a biocompatible electrical isolating material such as silicone, polyurethane, ceramics, PTFE or PEEK and/or comprises a flexible or resilient material.

However, to be more specific, examples of various materials for the embodiments of the stimulation media fixation unit include biocompatible thermoplastic materials such as Polyether-ketone based materials, HD-PE, PP, PET, Fluorinated polymer materials, or other sterilizable materials suitable for permanent contact through the skin of the patient. A metal-based version of a stimulation media fixation unit could be made from surgical steel like 316 LVM, titanium-based alloys and precious metal alloys. Additionally, ceramics may be used for shorter lengths and/or larger diameters of the stimulation media fixation unit member/s.

In an embodiment, the entire stimulation media fixation unit or the at least one electrode member/s are coated with precious metal alloys, titanium nitride or diamond like carbon in order to achieve better conductibility with high level biocompatibility.

In an embodiment, the coating constitutes a means for adjustment of the impedance at the tissue/electrode interface, and in other embodiments coatings promote tissue integration or cell adhesion. This could be achieved by designing a porous or partly porous stimulation media fixation unit body, combined with the desired coating material or materials for tailoring the desired properties of the complete assembled stimulation media fixation unit.

In an embodiment, the at least one of the first or second ends of the stimulation media fixation unit are configured with a part which forms a stop for moving the stimulation media fixation unit through the formed channel in the tissue in one direction. When the system is not activated the lead providing the stimulating signal can be removed entirely to allow the user to have maximum freedom from related inconveniences.

When the stimulation media fixation unit is initially inserted into the tissue, the end terminations of the stimulation media fixation unit form a stable fixation mechanism to the skin for having a fixed position specifying a fixed distance to the nerve of interest. Thus, the stimulation media fixation unit serves as a stable platform for arranging one or more electrodes for submitting a neuromodulation signal addressed to the nerve of interest. For securing the stimulation media fixation unit in the fixed position in the formed channel, at least one end termination arranged on the stimulation media fixation unit is provided to avoid that the stimulation media fixation unit can move out of the formed channel in the tissue in one direction. When inserted into the formed channel an end termination can be provided in the end not initially being equipped with an end termination providing a stop for movement in the other direction. The end termination can be provided in various ways.

It has to be understood that the end termination can be formed in various ways almost without any limits. However, considerations to the design need to address risks of infections if such would result in end termination designs that are difficult to maintain hygienically. Too pointy shapes and overly detailed objects may thus not be suitable as end termination, given the exemplified location at the genitals, as these may become difficult to maintain hygienic or at risk of harming the skin.

In an embodiment, the end termination is formed by configuring the end of the stimulation media fixation unit at least on a part of the first or the second end that is configured to protrude out of the formed channel with a cross-section that is larger than the measured circumscribed cross-section of the formed channel in such a way as to form a stop for movement of the stimulation media fixation unit through the formed channel in one direction.

In an embodiment, the end termination is formed by configuring the end of the fixation unit at least on a part of the first or the second end that is configured to protrude out of the formed channel with a thread for receiving a nut, said nut having a cross-section that is sufficiently larger than the measured cross-section of the formed channel in such a way as to form a stop for movement of the stimulation media fixation unit through the formed channel in one direction.

In an embodiment, the stop is provided by adding an end termination by snapping it onto the stimulation media fixation unit body. For the insertion and since the stimulation media fixation unit may need to be removed, it is possible to release the deflection/expansion and remove the end termination to allow an easy way in order to remove the stimulation media fixation unit out of the tissue, with no or only minimally invasive clinical intervention. The attachment of the end termination can include click-in features involving a spring member, or a magnet member, thread or similar interface between the end of the stimulation media fixation unit body and the end termination.

In embodiments, the end terminations to be arranged on the stimulation media fixation unit body ends can be designed in various ways, where one or all end terminations can be exchanged or interchanged to the preference of the wearer, to match for instances the skin or tissue color, or to match the size of the end termination to the preference of the user.

In an embodiment, the stimulation media fixation unit is designed to have two exchangeable end terminations of various designs for the preference of the wearer. The stimulation media fixation unit has two corresponding features of various designs to allow attachment of the electrode into or onto the stimulation media fixation unit.

In embodiments, the end terminations are threaded internally or have an external thread, which allows exchange of the end termination. Other forms of attachment include click-in features involving a spring feature, a snap feature or a magnet interface between the stimulation media fixation unit body and the end termination, where a magnet can be fitted internally into the stimulation media fixation unit.

In an embodiment, an end of the stimulation media fixation unit, at least on a part of the first and/or the second end that is configured to protrude out of the formed channel is configured with an interface for receiving a detachable end termination, the end termination being attached and secured in position by means of spring-loaded or magnetic force or click-in or by a threaded connection.

In a further embodiment, the stimulation media fixation unit, with or without attached end terminations, forms an electrical isolating member where the at least one electrode member or multiple electrode members are arranged on or in the stimulation media fixation unit in a position where the stimulation media fixation unit is adapted to be in contact with the tissue inside the formed channel through the skin.

In an embodiment, the at least one end termination comprises electrically isolating materials, such as PEEK, fluorinated materials, ceramics or similar nonconductive materials.

In another embodiment, the at least one end termination constitutes an electrical stimulating electrode utilizing conductive materials.

In an embodiment, an end termination constitutes a fixed feature having a suitable larger dimension with respect to the stimulation media fixation unit body on which it is arranged, providing a stop until the self-deflecting member arranged on or in the stimulation media fixation unit is sufficiently deflected/expanded.

In an embodiment, the stimulation media fixation unit comprises at least one detachable electrical connection providing the stimulation signal from a pulse generator to the at least one applied electrode.

In an embodiment, the system comprises an electrical connection between the electrode arranged on the stimulation media fixation unit and the pulse generator.

In various embodiments of the invention, the pulse generator is arranged in, on or with the stimulation media fixation unit.

In further embodiments, the pulse generator is connected to the stimulation media fixation unit via a detachable leaded connection. The pulse generator is in an embodiment arranged remotely from the stimulation media fixation unit.

In an embodiment, the system comprises a leaded electrical connection between the at least one electrode and the pulse generator and comprises further a connector configured for releasing the leaded electrical connection to the pulse generator when a preconfigured pull force is exceeded. The connection can be reobtained simply by re-connecting the leaded connection to the electrode fixation unit. The socket is in an embodiment a plug and socket connector. This is an appreciated behavior since pulling the electrode fixation unit when inserted into the tissue can be harmful or painful to the user. Thus, a safety arrangement as explained will simply decouple the lead and protect the user from harm at a designed level of forces.

In an embodiment, the electrode is supported in situ in a spring retained arrangement in such a way that when a preconfigured pull force is exceeded on the leaded connection, the electrode and/or the lead is released from its position on the electrode fixation unit. This is another solution for protecting the user against pulling the stimulation media fixation unit inserted the formed channel.

It has to be understood that electrical stimulation will need a signal to be provided through a first electrode, which will return to the pulse generator via a second connection or electrode. Thus, the invention also comprises a second electrode that in embodiments are arranged on the stimulation media fixation unit, or with the pulse generator serving as a counter electrode for the at least one electrode arranged on the stimulation media fixation unit. For embodiments equipped with a vibration generator, additional signaling and powering of the vibration generator is required.

Fixating stimulation electrodes in position through the skin by using a stimulation media fixation unit adapted to be expandable or deflectable in a formed channel in the living being leaves out concerns of migration. Electrode dislocation, in relation to the nerve of interest, has fatal consequences for the efficacy of the system, and such risks are further mitigated by providing means of forming the electrodes when positioned in the formed channel through the skin, and in some embodiments additionally providing elements for fibrosis entanglement. The establishment of a stable nerve electrode interface is of crucial importance for systems applying electrical stimulation of nerves and this additionally increases the efficiency of vibrations stimulation applied in order to treat physical disorders.

BRIEF DESCRIPTION OF THE DRAWINGS

For the purpose of illustrating the invention, forms are shown in accompanying drawings, which are presently preferred, it being understood that the invention is not intended to be limited to the precise arrangements and instrumentalities shown. The invention includes.

DETAILED DESCRIPTION

Figure 1:
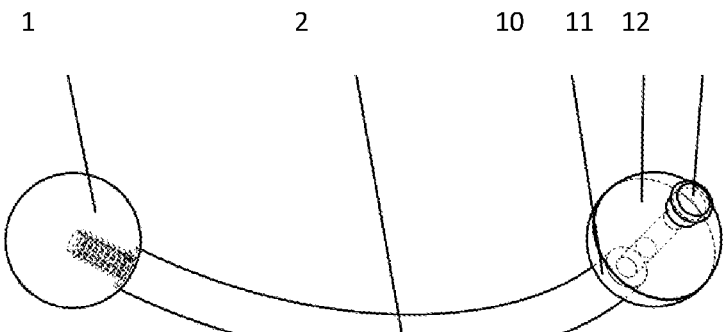
FIG. 1, illustrates a smoothly bended embodiment of the stimulation media fixation unit body (2) with one end termination (1) attached using threads and one end termination magnetically attached (10). The latter end termination allows for electrical connection (11 and 12) via a connector and lead to a pulse generator, with no deflectable member attached.

FIG. 1 represents an example of a stimulation media fixation unit body (2) constituting the at least one electrode member and with no added deflectable member/s, where the method of end termination (1) attachment is shown using threads. The stimulation media fixation unit body (2) can be solid as well as hollow. Hollow embodiments having a suitable straight internal section can be equipped with a vibration generator constituting an efficient solution for mechanically vibrations stimulation. However, the internal features inside the stimulation media fixation unit may be fit for squarish vibration generator member/s. The vibrating motors should preferable be encapsulated and waterproof, otherwise water proofing details are incorporated into the stimulation media fixation unit at the end terminations. It has to be understood that the mode of vibrations is only exemplified as rotational movements, and thus may be as well be based on linear resonant actuation, and further the mode of vibration is not limited to sinusoidal vibrations, but can be inhomogeneous, including, shaking or shivering and have various amplitudes and acceleration factors, by use of haptic linear resonators.

The end terminations (1, 10) could as well be clicked-in, magnetically attached, spring loaded or attached using similar concepts. The shape or design of the end terminations (1, 10) is preferably round and ball-shaped to be the least sharp as possible, and to allow easy hygienically maintenance and thus avoid infectious circumstances. Other designs are optional if they are hygienically acceptable and does not constitute a risk of harm for the surrounding tissue.

The shape of the stimulation media fixation unit body (2) can vary, having the goal to position the electrodes members/s configured on the stimulation media fixation unit or being an integral part/s of or add-on's to the stimulation media fixation unit, close to the targeted nervous tissue for optimal stimulation efficacy. Therefore, the bending radii and bending angles are configured or selected in accordance with the specific stimulation site of interest. The preferred cross sections of the stimulation media fixation unit body (2) are ranging from ø1 mm to ø6 mm, although not necessarily being circular. Sections of the stimulation media fixation unit body having larger diameter, i.e. up to 10 mm, could be optional where a large charge injection is important for the application, or high level of vibrations energy is required. The preferred stimulation media fixation unit body lengths are from 10 mm to 40 mm and should be anatomically feasible for the site at which the electrode fixation unit shall function. The length of the electrode fixation unit body can be up to for up to 100 mm. If longer distances of fixation are necessary, application of additional stimulation media fixation units are preferable. The curvature and length of the stimulation media fixation unit determines the depth of the stimulation media fixation unit into the tissue. The requirement for how profound the stimulation media fixation unit can be positioned vary depending on the local tissue at the site of interest, considering among other things the length of the stimulation media fixation unit body, the cross section etc., and the anatomical location of the stimulation media fixation unit. If the stimulation media fixation unit is too small, the quality of the fixation will drop, with subsequent increased risk of compromised electrode/tissue interface e.g. loss of performance or function.

FIG. 1 represents one shape of the stimulation media fixation unit body (2). Further designs could include bended and coiled wires constituting the stimulation media fixation unit body (2), providing additional means of fixation into the tissue. Similarly, sharper bended stimulation media fixation unit body (2), multi-axis curved stimulation media fixation unit designs are optionally solutions for additional fixation.

FIG. 1 shows a stimulation media fixation unit body design (2) utilizing magnetic end termination support (10) for the electrical connected end termination (11 and 12), consisting of an isolating or conducting lower section (10), and isolating upper section (11), and the connector detail (12) for the lead connection. The isolating materials of the end termination/s (10, 11), when designed not to be part of the electrode member/s, can comprise PEEK, fluorinated materials, ceramics or similar biocompatible materials. The outer surface of the stimulation media fixation unit body (2) becomes the electrode interface to the tissue. When the lower section (10) of the end termination are part of the electrode interface, this part is then designed utilizing 316L or precious metals suitable for the application. Thus, the stimulation media fixation unit body (2) and/or the at least one end termination (1, 10) constitutes an electrical stimulating electrode member.

Figure 2:
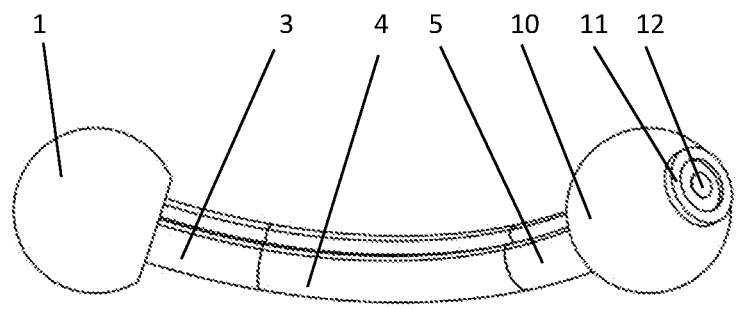
FIG. 2, illustrates a stimulation media fixation unit similar to the one in FIG. 1, with at least one end termination having integrated connection details (11 and 12), and an adjustable end termination (1) controlling the degree of deflection of the deflectable members, and attached deflectable members presented in the non-deflected state, where the stimulating electrode (4) is positioned between one deflectable element (5) at the first end, and another deflectable element (3) in the second end, and where the deflectable elements need not have similar properties.
Figure 3:
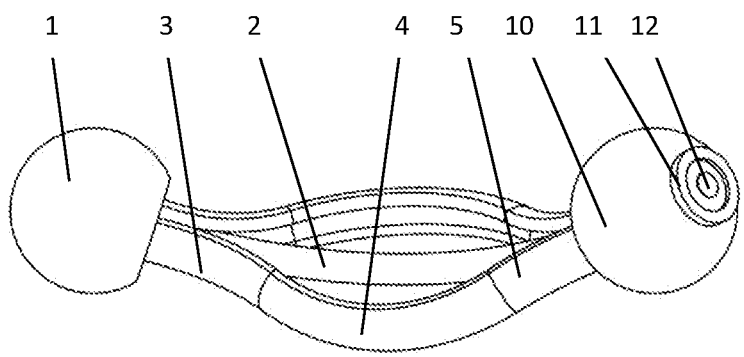
FIG. 3, illustrates the stimulation media fixation unit of FIG. 2, where the deflectable members are presented in a deflected state.

FIG. 2 and FIG. 3 represents a stimulation media fixation unit body with an end termination (1) controlling the degree of deflection of the deflectable member/s (3 and/or 4 and/or 5) attached to either side of the stimulation media fixation unit body (2), presented in closed and open state respectively. The deflectable member/s (3 and/or 4 and/or 5) could as well be positioned below and/or above, in fact in any angle around the electrode fixation unit body (2), for applications when a specific position of the deflectable member/s (3 and/or 4 and/or 5) would be beneficial for targeting nervous tissue at the specific site of stimulation.

The deflectable member/s (3 and/or 4 and/or 5) constitute either an electrode member and/or a fixation member of the stimulation media fixation unit. In embodiments where the at least one deflectable member/s (3 and/or 4 and/or 5) constitute non-conductive fixation member/s, the stimulation media fixation unit body (2) constitutes at least one electrode member as an integrated stimulation electrode member in a monopolar configuration. Miniaturization of the active part of the electrode member/s is limited by the charge storage capacity and impedance of currently applied materials. A monopolar configuration maximizes the optional area available for electrode member/s relative to the stimulation media fixation unit body length and cross section of the stimulation media fixation unit body, as it need not share the available surface area with a second, third or multiple electrode member/s (4). Larger charge input may thus require longer stimulation media fixation unit body designs (2) to obtain larger electrode surfaces.

In another embodiment, the at least one deflectable member (3 and/or 4 and/or 5) constitute a non-conductive fixation member, and the stimulation media fixation unit body is designed in a bipolar electrode configuration having two electrode member/s, it is required to have an isolation member positioned in-between the at least two electrode members, where the isolating material between the at least two electrode members shall be biocompatible or bio-inert, of which PEEK or ceramics are ideal. Other materials could include fluorinated based materials. Thus, the stimulation media fixation unit body has sections that are intended to be not electrically conductive. Tri-polar, quadrupolar or 5-polar electrode concepts could also prove to be relevant options in some applications, although such configurations are not included in the illustrations. The shapes of the stimulating electrode areas are of limited importance but should be smooth enough to allow insertion and prevent sharp edges that may become irritant or even unsafe in the formed channel in the tissue. The size of the electrode areas is balanced with the load of charge to be injected, the electrode material chosen, and frequency of use of the application applied. A feature for electrical contact is shown as a dual magnetic connection (11, 12), but other designs are also relevant, utilizing, spring loads or click-in etc.

The degree of deflection of the deflectable members/s (3 and/or 4 and/or 5) of the either conductive or non-conductive member/s of the stimulation media fixation unit is controlled by strain added to the deflectable elements (3 and/or 4 and/or 5). The level of strain is controlled by relative movement of the first end termination (1) to the second end termination (10), forcing the deflectable member/s (3 and/or 4 and/or 5) to bend outwards away from each other. The mechanism can be provided in various ways, by turning a thread, clicking features, or frictionally controlled.

The deflectable member/s (3 and/or 4 and/or 5) will determine the deflection shape of the deflectable member/s when activated. The materials and designs applied shall be flexible enough to be controlled by the mechanism means applied but should be rigid enough to maintain a stable position once deflected.

It is important that the stimulation media fixation unit body (2) is stiff or rigid enough to withstand the resultant force required to deflect the one or more deflectable member/s (3 and/or 4 and/or 5). The stimulation media fixation unit body (2) could be made entirely from conductive or non-conductive materials, or both. The electrode fixation unit body (2) can be solid as well as hollow and when having a suitable straight internal section, the electrode fixation unit body can be equipped with a vibration generator (16) constituting an efficient solution for mechanically vibrations stimulation.

The clinical success of electrical stimulation-based systems depends among other things on the ability of the electrode contact to consistently provide safe levels of stimulation to the target component of the nervous system. Exceeding the limit for safe charge injection may cause electrode degradation and/or irreversible tissue damage resulting in loss of clinical efficacy and the electrode becoming unsafe. To mitigate the problems associated with reduced physical size, advanced biomaterials and precious materials can be used to ensure longevity. The electrode member/s (3 and/or 4 and/or 5) are the electrochemically active areas of the electrodes where charge transfer occurs during stimulation. The electrode member/s (3 and/or 4 and/or 5) is supposed to be in close proximity of the target nerve to obtain low stimulation thresholds. Ideally, the electrode member/s (3 and/or 4 and/or 5) should have good chemical stability, high charge injection capacity, low electrical impedance, and should remain inserted in the tissue as a compliant material causing low degree of inflammation.

Figure 4:
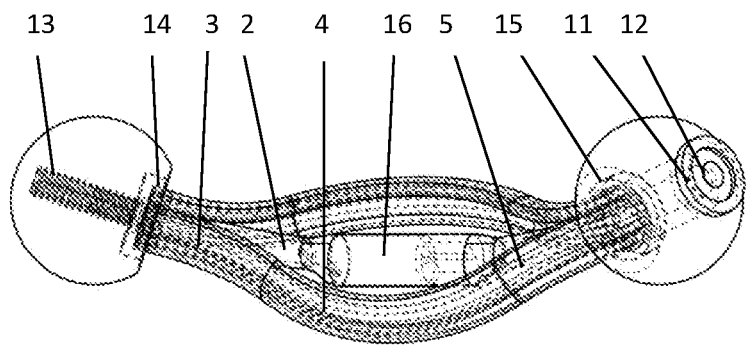
FIG. 4, illustrates internal features of an embodiment of the stimulation media fixation unit holding a vibration generator, and including a mechanism for controlling the degree of the deflection of the deflectable members, by means of threaded components (3, 4 and 5)

FIG. 4 represents a stimulation media fixation unit including a vibrations generator (16) and showing further details of an end termination positioned in the first end (13) controlling the degree of deflection of the deflectable member/s attached to either side of the stimulation media fixation unit, by means of threads.

The first end termination (13) is moved closer to the static connector end termination positioned in the second end, thus adding strain to the at least one deflectable member (3 and/or 4 and/or 5) when turned, pushing an anchor-member (14), which is guided in a tongue groove hindering the at least one deflectable member (3 and/or 4 and/or 5) to twist around the stimulation media fixation unit body (2), to deflect the at least one deflectable member/s (3 and/or 4 and/or 5). At the second connector end termination, a static anchor-member (15) provides rotational fixation of the deflectable member/s (3 and/or and/or 5). The pitch of the thread in the first end termination (1) determines relative movement of the moving end termination (1) per turn, relative to the static connector end termination in the second end. The static connector end termination includes connection details for the electrical pulse generator and/or the vibration generator (16) for vibrations stimulation.

The compression distance i.e. the distance of linear travel of the moving end termination (1) relative to the static connector end termination shall be planned during the implantation procedure performed in the clinical facility.

Figure 5:
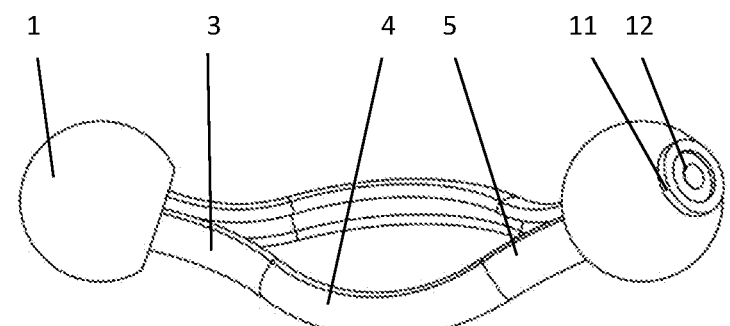
FIG. 5, illustrates an embodiment where the deflectable members constitute the stimulation media fixation unit body, and where the deflection is provided by means of shape memory alloy (e.g. nitinol)

FIG. 5, represents a stimulation media fixation unit, where the deflectable members (3 and/or 4 and/or 5) constitutes the stimulation media fixation unit body, and are self-deflective controlled by means of relative temperature change of shape memory alloy such as nitinol. The end termination (1) can be repeatably dismantled and assembled to the electrode fixation unit by means of e.g. threaded details.

The degree of deflection is predetermined by the design of the shape memory alloy member. During the clinical procedure, the stimulation media fixation unit is cooled to collapse into the most elongated shape as illustrated in FIG. 2, thus prepared for the insertion into the formed channel through the skin. As the stimulation media fixation unit reaches the body temperature, the at least one deflectable member/s (3 and/or 4 and/or 5) of the stimulation media fixation unit returns to the predetermined shape as designed into the shape memory alloy.

In order to design bipolar versions of the embodiment presented in FIG. 5, the parts (3 and 5) of the deflectable member/s (3 and/or 4 and/or 5) are isolated from the middle section (4). This can be achieved in various way, the simplest by addition of conductive coating of a suitable length of the elements (3 and 5), and resultantly providing enough electrode area (4) for the therapy planned. In other designs, either of the two deflectable member/s (3 and/or 4 and/or 5), constitute an anode or cathode respectively, where the middle section (4) becomes the electrode member/s, arranged between isolation member/s (3 and 5).

Figure 6:
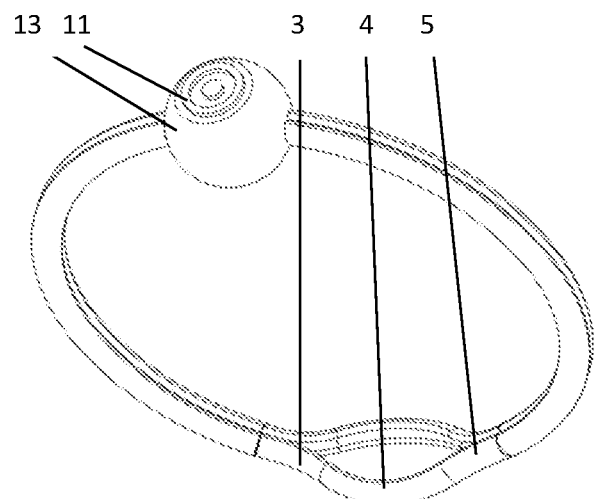
FIG. 6, illustrates an embodiment of a stimulation media fixation unit of complete closed ring design, where the deflectable members partially constitute the stimulation media fixation unit body, and where the deflection is provided by means of shape memory alloy (e.g. nitinol)

FIG. 6, illustrates a stimulation media fixation unit having a closed-loop stimulation media fixation unit body shape, here presented as a circular unit. The end termination (13) is formed by use of a single end termination member, utilizing spring loaded end termination fixation arranged into carved features in the stimulation media fixation unit body. The stimulation media fixation unit body need not be circular and the end termination (13) need not have a shape identical to the stimulation media fixation unit body onto which it is arranged but can have an identical or similar design becoming a circular endless ring. The end termination (13) and the stimulation media fixation unit body have a smooth surface and overall structure for at least the part positioned or arranged inside the formed channel in the tissue. The stimulation media fixation unit body includes at least one deflectable member (3 and/or 4 and/or 5) constituting a structural element hindering the stimulation media fixation unit to rotate within the formed channel and providing means for tissue integration within the formed channel through the skin.

The degree of deflection is predetermined by the design of the shape memory alloy. During the clinical procedure, the stimulation media fixation unit is cooled to collapse into the shape as illustrated in FIG. 2, thus prepared for the insertion into the formed channel in the skin. As the stimulation media fixation unit reaches the body temperature, the at least one deflectable member of the stimulation media fixation unit returns to the predetermined shape as designed into the shape memory alloy, leaving no compression distance to be considered during the planning of the clinical procedure.

Figure 7:
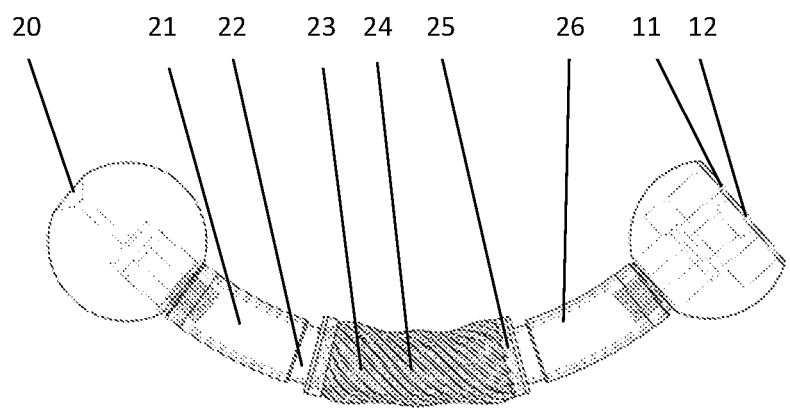
FIG. 7, illustrates a stimulation media fixation unit, with at least one end termination having integrated connection details (11 and 12), and an end termination specially adapted for pressurization of a build in balloon (24) controlling the degree and shape of deflection of the deflectable member/s (23), and an attached deflectable electrode member (23) presented in the non-deflected state, where the electrode members (21 and 26) are positioned on either side of the deflectable electrode member (23)
Figure 8:
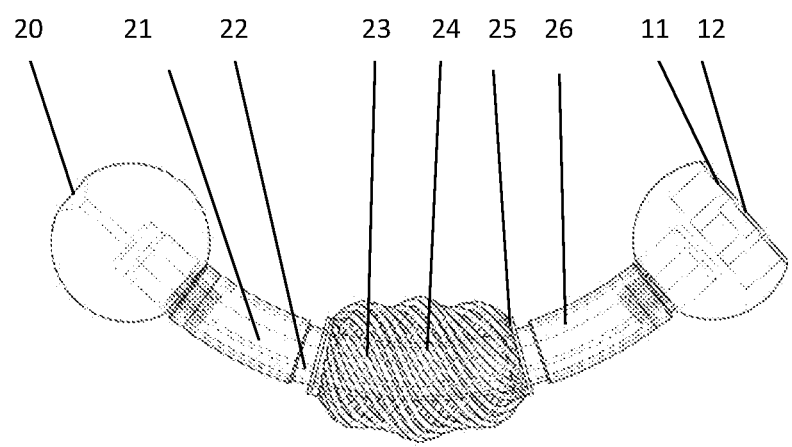
FIG. 8, illustrates the stimulation media fixation unit of FIG. 7, where the deflectable member (23) is presented in a deflected state.

FIG. 7 and FIG. 8 illustrates an embodiment of a stimulation media fixation unit utilizing a pressurized balloon type mechanism for activating at least one deflectable member (23), presented in the non-deflected and a deflected state respectively. The shape of the deflectable member/s (23) once inflated, or expanded using a liquid, is controlled by the shape of the balloon (24) and the pressure/volume inflated/ filled into the balloon (24), and the fixture-element member (25) provided in both the first and second end of the deflectable member/s. In embodiments including two moveable or non-moveable fixture-elements (25), the deflectable member/s (23) forms a ball-like volume, being rounded triangular, squarish or multiple angled cross sectional until substantially being wholly round ball-shaped or various ellipsoidal shapes. In embodiments utilizing a single fixture-element member (25), the shape of the deflectable member/s (23) becomes rounded triangular, squarish or multiple angled cross-sectional representations of umbrella-shapes. Further in embodiments utilizing sets of at least two singular fixture-elements (25), the at least two deflectable members (23) each forms an umbrella shape.

The balloon member (24) is pressurized or inflated through an inlet in the first passive end termination member (20) and controlled by means of the volume filled into a syringe, or by use of available laboratory equipment, having a suitable tip fitting to the inlet details in the first end termination member (20).

There are provided access from the inlet in the first end termination member (20) through any attached external electrode member (21) and to the balloon member (24), which inflates and deflects the at least one deflectable member (23). The at least one fixture-element member (25) fixates the at least one deflectable member (23) radially, and in some embodiments additionally longitudinally on the stimulation media fixation unit. An isolation member (22) is added for embodiments where the deflectable member (23) is configured as an active stimulating electrode.

In embodiments including sufficient length of internal straight section, a vibration generator is positioned within the electrode member (26), which need not be pathway for operating the balloon member (24). The deflectable member/s (23) can be made from various types of metallic or at least conductive meshes and/or wire-based hoses and be loosely attached to the electrode fixation unit once deflected, to form a deflectable electrode member promoting fibrotic tissue entanglement for optimal electrode and vibration performance.

Further, the mesh, wire or hoses as described could as well be manufactured from various types of non-conductive fabrics or polymers, functioning exclusively as non-active fixation member/s.

Figure 9:
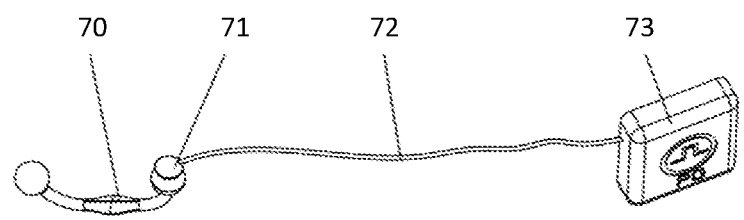
FIG. 9, illustrates an example of the entire system, where the electrode fixation unit (70) could be either one of the above presented stimulation media fixation units.

FIG. 9 shows an example of an entire electrical stimulation system, represented by the electrode fixation unit (70) of any of the above described embodiments. The lead (72) is detachable and is designed to release connection (71) at a predetermined force, the preferred method of connection being magnetically support. A similar connection can be arranged on the pulse generator (73). The lead holds at least the corresponding number of wires as the stimulation media fixation unit holds electrodes, and if also equipped with a vibration generator additional wires for powering said vibration generator, and hence any of the previous systems illustrated in FIG. 1 to FIG. 8 could constitute the stimulation media fixation unit (70) as shown in FIG. 9.

The invention claimed is:

1. A stimulation media fixation unit for electrical and/or mechanical stimulation of a nerve of a living being configured to be arranged in a channel formed into and out of the skin of the being, the stimulation media fixation unit including:
    at least one electrode and/or at least one vibration generator configured to be placed in close proximity of a portion of the nerve of the living being;
    a pulse generator configured to provide a sequence of electrical pulses to the at least one electrode or the at least one vibration generator in order to achieve stimulation of the nerve, the at least one electrode being configured to deliver electrical stimulation to the nerve, the at least one vibration generator being configured to deliver mechanical vibrations to the nerve;
    a first end and a second end, wherein the first end of the stimulation media fixation unit is configured to protrude out of a first end of the channel and the second end of the stimulation media fixation unit is configured to protrude out of a second end of the channel;
    at least one end termination member configured to be dismantled from and reassembled to the stimulation media fixation unit, the at least one end termination member being configured to provide a stop for movement of the stimulation media fixation unit in at least one direction within the channel, wherein the at least one end termination member is adapted to be positioned outside the first and/or second end of the channel and comprises a mechanically interlocking mechanism comprising a geometry that is configured to maintain the stimulation media fixation unit in the channel; and
    at least one expanding member and/or at least one adjustable deflectable electrode member adapted to anchor the unit in the channel.

2. The stimulation media fixation unit according to claim 1, wherein the deflectable member has a degree of deflection/expansion that is at least 20% relative to the initial dimension it expands.

3. The stimulation media fixation unit according to claim 1, wherein the electrode fixation unit has an elongated form, the electrode fixation unit having a first end and a second end where the first end of the electrode fixation unit is configured to protrude out of the channel in the tissue through a first perforation of the skin and the second end is configured to protrude out of a second perforation of the skin of the channel formed by two interconnected perforations of the skin of the living being when said electrode fixation unit is inserted into said channel, into which the fixation unit is configured to be deformed/deflected and thus adapted to mechanically anchor and interlock into the tissue.

4. The stimulation media fixation unit according to claim 1, wherein the stimulation media fixation unit includes an internally elongated form and comprises a mechanical expansion mechanism adapted to maintain effective transfer of vibration energy in the form of sinusoidal, linear, rotational, shaking, shivering, haptic movements or random vibration of various amplitudes and frequencies to the targeted tissue, when the stimulation media fixation unit is arranged in the channel.

5. The stimulation media fixation unit according to claim 1, wherein the stimulation media fixation unit is solid, hollow or tubular in form, and the cross section has a triangular, square or multiple-angled cross section; is substantially circular or elliptical in form with even or uneven sized sides; and/or with straight or curved sides and having one or multiple cross sectional areas over its length between the first end and second end and where the electrode fixation unit can travel in a straight, bended, curved, spiral, meandering or a combination of such travel forms in the longitudinal direction.

6. The stimulation media fixation unit according to claim 1, wherein the stimulation media fixation unit is holding the at least one vibration generator for vibrations stimulation, the stimulation media fixation unit being adapted to form a hollow tube fitting the at least one vibration generator, the stimulation media fixation unit further comprising a first end termination having an electrical connection to a pulse generator, a second passive end termination fitted at the second end of the stimulation media fixation unit, and at least one deflectable fixation member comprising a nickel titanium based material having shape-memory effect, such as nitinol.

7. The stimulation media fixation unit according to claim 1, wherein the deflectable member of the stimulation media fixation unit which comprises a material with shape-memory effect, has a deflection state which is temperature controlled to form itself into a predetermined body shape by means of elevation of the temperature from a level in the range between 0-10 degrees Celsius to a level in the range between 30-40 degrees Celsius, which can be achieved by means of heating by body temperature once positioned into the channel.

8. The stimulation media fixation unit according to claim 1, wherein the stimulation media fixation unit is partly made of an electrical isolating material having electrical conductible sections which serves as electrode member/s suitable for electrical stimulation, having a hollow fixation member with electrical connection/s to the electrode/s running internally in the stimulation media fixation unit and which are terminated in a connector accessible from outside of the stimulation media fixation unit and at least one deflectable/expandable electrode member securing the positioning of the electrode member in the channel, by means of tightening the passive end termination member to expand/deflect the deflectable/expandable electrode member to the degree tolerable by the user.

9. The stimulation media fixation unit according to claim 1, wherein at least one electrode member/s is arranged on the stimulation media fixation unit, and further comprises a deflectable electrode member comprising a nickel titanium based alloy having temperature controlled shape-memory effect, such as nitinol, where the deflectable member is configured to collapse into a closed form in an environment having a temperature level in the range between 0-10 degrees Celsius and thus being prepared for insertion into the channel in which it reaches the surrounding temperature of between 30-40 degrees Celsius and thereby return itself into the intended predetermined shape in the channel.

10. The stimulation media fixation unit according to claim 1, wherein the at least one deflectable member of the stimulation media fixation unit is constituting a passive or non-active fixation member, i.e. not part of, or including an electrode member, where the electrode member is arranged on the stimulation media fixation unit body.

11. The stimulation media fixation unit according to claim 1, wherein the at least one deflectable member constitutes an electrode, an anode, a cathode, a non-active fixation means or a combination thereof.

12. The stimulation media fixation unit according to claim 1, wherein the deflectable member of the stimulation media fixation unit is configured to be transformed into the intended shape by control of the deflectable member through turning a threaded end termination member positioned on the stimulation media fixation unit, shortening the distance between the first end termination and the second end termination and thus causing the deflectable member to bend from its initial shape.

13. The stimulation media fixation unit according to claim 1, wherein the at least one deflectable member is arranged on the stimulation media fixation unit and configured to be transformed into predetermined deflected shape through means of shortening the distance between the first end termination and the second end termination by configuring the first end termination to travel along the stimulation media fixation unit body, where dents positioned on the stimulation media fixation unit body define the travel distance/s and a spring loaded mechanism in the first end termination member fixates the end termination in at least two positions.

14. The stimulation media fixation unit according to claim 1, wherein the deflectable member further comprises a balloon arranged with the deflectable member where the deflectable member is configured to be formed by means of the balloon, pressurized for expanding and shaping a ductile deflectable fixation and/or electrode member.

15. The stimulation media fixation unit according to claim 1, wherein the deflectable member features balloon expansion and includes a flexible sheet or tube element added onto the outside or into the inside of the deflection member, the flexible sheet being adapted for avoiding tissue integration into the deflection member.

16. The stimulation media fixation unit according to claim 1, wherein the flexible conductive element is made of or includes conductive materials and is formed by one or more of plate springs, rod springs, coiled springs, or ductile elements which are at least partially maintaining the deflected shape, once the force providing the deflection is released.

17. The stimulation media fixation unit according to claim 1, wherein the at least one end termination member is attached to an end of the stimulation media fixation unit body, but with a gap between the end termination member and the other end of the stimulation media fixation unit body featuring or not featuring another end termination member.

18. The stimulation media fixation unit according to claim 1, wherein the stimulation media fixation unit comprises at least one detachable electrical connection providing the stimulation signal from a pulse generator to the at least one applied electrode.

19. A system for stimulation of nerves including the stimulation media fixation unit according to claim 1, wherein the system comprises an electrical connection between the electrode arranged on the stimulation media fixation unit and the pulse generator.

20. A system for stimulation of nerves including the stimulation media fixation unit according to claim 1, wherein the pulse generator is arranged in, on or with the stimulation media fixation unit.

* * * * *